United States Patent [19]

Taira et al.

[11] Patent Number: 5,861,034
[45] Date of Patent: Jan. 19, 1999

[54] ARTIFICIAL DURA MATER

[75] Inventors: Tsuguyoshi Taira; Shinichiro Morita, both of Ayabe; Yoshito Ikada, Uji, all of Japan

[73] Assignee: Gunze Limited, Kyoto-fu, Japan

[21] Appl. No.: 824,829

[22] Filed: Mar. 26, 1997

[51] Int. Cl.$^6$ ..................................................... A61F 2/02
[52] U.S. Cl. ............................. 623/11; 606/77; 606/154; 600/37
[58] Field of Search ................................ 623/11; 606/77, 606/151, 154; 600/37; 523/113

[56] References Cited

U.S. PATENT DOCUMENTS

| | | | |
|---|---|---|---|
| 4,045,418 | 8/1977 | Sinclair | 528/357 |
| 4,655,203 | 4/1987 | Tormala et al. | 623/16 |
| 4,968,317 | 11/1990 | Tormala et al. | 606/77 |
| 5,250,584 | 10/1993 | Ikgda et al. | 623/16 |
| 5,304,377 | 4/1994 | Yamada et al. | 424/426 |
| 5,522,895 | 6/1996 | Mikos | 623/16 |
| 5,674,286 | 10/1997 | D'Alessio et al. | 623/11 |
| 5,747,637 | 5/1998 | Shinoda et al. | 606/154 |

FOREIGN PATENT DOCUMENTS 000499204  8/1992  European Pat. Off. ................ 606/77

OTHER PUBLICATIONS

Abstract of Japanese patent application No. JP 63305046 published Jun. 12, 1990.

*Primary Examiner*—Paul B. Prebilic
*Attorney, Agent, or Firm*—Hardaway Law Firm P.A.

[57] ABSTRACT

The invention provides an artificial dura mater comprising a sheet made of bioabsorbable synthetic polymers formed from copolymers of lactic acid and $\epsilon$-caprolactone.

2 Claims, No Drawings

ARTIFICIAL DURA MATER

INDUSTRIAL FIELD

The invention relates to an artificial dura mater which is used for prosthesis of defect of dura mater in a field of neurosurgery.

BACKGROUND ART

Dura mater occuring between skull and brain protects the brain and inhibits leakage of cerebrospinal fluid. A defect or a contracture of dura mater may be filled with lyophilized products of human dura mater.

However, said lyophilized products of human dura mater have drawbacks such as low homogeneity, short supply, viral infection (Noshinkeigeka; 21(2), 167–170, 1993) and poor biocompatibility with tissue surface due to hardness.

Artificial dura mater made of silicone was developed to solve these drawbacks. However, silicone dura mater, which is not biodegradable, remains in vivo permanently and stimulates peripheral tissue leading to enlargement of granulation tissue and increase of meningorrhagia. Because of these drawbacks, silicone dura mater is disfavored.

In contrast, artificial dura mater made of biodegradable materials, such as collagen (*Journal of Biomedical Materials Research*; Vol. 25, 267–276 (1991)) and gelatin (Brain and Nerve (No to Shinkei), 21, 1089–1098 (1969)) is not in practical use due to a lack of sufficient strength to suture internal dura mater and artificial dura mater integrally. Human dura mater lyophilized products with the stated drawbacks are, therefore, used because of lack of substitutes.

It is an object of the invention to provide an artificial dura mater free of drawbacks, with sufficient strength for suture, softness so as not to damage a brain surface, modulus of elasticity close to the native dura mater, superior biocompatibility, and biodegradability accompanying repair of damaged tissue.

DISCLOSURE OF THE INVENTION

The invention provides an artificial dura mater comprising a sheet made of biodegradable and bioabsorbable synthetic polymer or polymers.

The biodegradable and bioabsorbable synthetic polymer (or polymers) comprises a copolymer of lactic acid and ε-caprolactone.

The artificial dura mater may further comprise a sheet made of biodegradable and bioabsorbable synthetic polymer or polymers integrated with reinforcement which may be a fiber component.

The invention is novel in that dura mater is made of biodegradable polymer or polymers such as polyglycolic acid, polylactic acid, or poly-ε-caprolactone (which is a hydroxycarboxylic acid), and that the polymers are suitably blended.

The sheet of the invention may be prepared by air-drying or freeze-drying a solution of a copolymer of lactic acid and ε-caprolactone cast on an open type mold or by hot-pressing a copolymer of lactic acid and ε-caprolactone. The sheet of the invention may also be prepared by melt extrusion or injection molding of a copolymer of lactic acid and ε-caprolactone. A molar ratio of lactic acid between 25–60% and a molar ratio of ε-caprolactone between 75–40% is preferred. However, a molar ratio of 50% lactic acid and 50% ε-caprolactone has been found to provide a low modulus of elasticity as well as softness suitable for an artificial dura mater.

As the molar ratio of lactic acid increases, the copolymer becomes hard and the modulus of elasticity increases. Similarly, as the molar ratio of ε-caprolactone increases, the modulus of elasticity of the copolymer increases leading to an increased possibility of damage to the brain surface.

A thickness of the sheet is easily controlled by adjusting the concentration of the copolymer solution, the amount of solution for casting, or the pressure in hot-pressing. When the sheet is too thin, artificial dura mater may leak cerebrospinal fluid due to low strength. When the sheet is too thick, rigidity thereof increases leading to damage of the brain surface.

An adequate thickness of the artificial dura mater, with required strength, ranges between 50–800 μm.

Reinforcement may be introduced between sheets made of a copolymer of lactic acid and ε-caprolactone. The reinforcement is integrated with the sheet of the invention. Reinforcement may be a mesh, knit, woven fabric or nonwoven fabric made of bioabsorbable polymer, such as poly-ε-caprolactone, polylactic acid, polyglycolic acid, a copolymer of lactic acid and ε-caprolactone, a copolymer of glycolic acid and ε-caprolactone, a copolymer of glycolic acid and lactic acid or a mixture thereof.

A first preferable reinforcement is not dissolvable in the solvent in which the sheet of the invention is dissolved. This first reinforcement includes polyglycolic acid. A second preferable reinforcement has a higher melting point than a sheet made of biodegradable and bioabsorbable synthetic polymer or polymers. This second reinforcement and sheet may be made of a copolymer of lactic acid and ε-caprolactone with different proportion of lactic acid and ε-caprolactone. This second reinforcement and sheet may also be made of different biodegradable polymers. A thickness of reinforcement preferably ranges between 50–200 μm for integration with the film sheet.

The artificial dura mater with reinforcement increases suture strength and decreases dilation of pinhole during suture.

The dura mater of the invention meets all requirements such as non-leakage of cerebrospinal fluid, sufficient strength for suture, softness so as not to damage the brain surface, modulus of elasticity close to the native dura mater, superior biocompatability, and biodegradability accompanying repair of damaged tissue. In addition, the artificial dura mater is transparent so that internal conditions may be observed through the artificial dura mater, which is useful for detecting trouble in the early stage. The artificial dura mater, capable of production in on industrial scale, is less expensive, more stable, and higher in quality than lyophilized products of human dura mater.

The invention will be described below in detail in view of the examples.

BEST MODE FOR CARRYING OUT THE INVENTION

Example 1

Lactic acid and ε-caprolactone copolymer (50:50, molar ratio) having a molecular weight of 370,000 was hot-pressed at 110° C. under 160 kg/cm² and then quenched in water to obtain an artificial dura mater of the invention with a film sheet having a thickness of 250 μm.

Example 2

Lactic acid and ε-caprolactone copolymer (50:50, molar ratio) having a molecular weight of 370,000 was hot-pressed at 110° C. under 190 kg/cm² and then quenched in water to obtain an artificial dura mater of the invention with a film sheet having a thickness of 100 μm. An unwoven fabric sheet prepared by plain-knitting a polyglycolic acid yarn having 15 deniers, and needle-punching the plain knit sheet, was sandwiched between two said film sheets made of lactic acid and ε-caprolactone copolymer. The laminated sheets were again hot-pressed at 110° C. under 190 kg/cm² and then quenched in water to obtain an integrated artificial dura mater of the invention having a thickness of 220 μm.

<Performance Assessment>

1. Evaluation test of physical properties:

Physical properties of artificial dura mater of the invention obtained in examples 1 and 2, human native dura mater, and human lyophilized dura mater were determined.

Each test was repeated 5 times to calculate the mean value of each physical property.

(1) Tensile strength test

A test piece (5 mm×60 mm) was drawn under conditions of chuck distance (10 mm) and rate of pulling (100 mm/min).

(2) Suture strength test

Two sutures (3-0 size) passed a test piece (7 mm×10 mm) at the site of 3 mm distant from both ends. The sutures were pulled from both sides to measure breaking strength.

(3) Flexural rigidity test

Flexural rigidity of a test piece (5 cm×8 cm) was measured with a bending test machine (KES-FB2). The results are shown in table 1. The artificial dura mater of the invention meet strength and softness required in the application. In particular, the artificial dura mater obtained in example 2 containing reinforcement has a higher suture strength, which implies non-leakage of cerebrospinal fluid after suture. Flexural rigidity of artificial dura mater of the invention is lower than conventional dura mater showing softness thereof.

The human native dura mater, as a control; was obtained from human body by ablation during operation. The human lyophilized dura mater, as control, was a commercially available product (LYODURA; product of B. Braun Co., Ltd.).

TABLE 1

|  | Thickness (μm) | Tensile strength (MPa) | Suture strength (MPa) | Flexural rigidity (gf cm²/cm) |
|---|---|---|---|---|
| Example 1 | 250 | 14.88 | 1.77 | — |
| Example 2 | 220 | 11.40 | 6.42 | 0.4637 |
| Human native dura mater | 626 | 8.80 | 1.90 | — |
| Human lyophilized dura mater | 551 | 11.93 | 2.32 | 0.6215 |

(n = 5)

2. In vitro degradation test

Each test piece (5 mm×80 mm) of the artificial dura mater obtained in example 2 was dipped in physiological saline at 37° C. for 1, 7, 15, 21 or 30 days. Subsequently, the test pieces were subjected to a tensile strength test. The results are shown in table 2.

TABLE 2

| Dipping period (day) | Tensile strength (kgf) |
|---|---|
| Initial | 1.02 |
| 4 | 1.01 |
| 7 | 0.94 |
| 15 | 0.51 |
| 21 | 0.43 |
| 30 | 0.28 |

Tensile strength of the test piece is halved after dipping in physiological saline for 2 weeks showing that the artificial dura mater will be degraded in vivo.

Coat is usually formed within one month after operation so that leakage of cerebrospinal fluid is inhibited. Dura mater is recovered on the coat. Therefore, the degradation pattern of the sheet obtained in example 2 is suitable for artificial dura mater.

2. In vivo degradation test

Test pieces (5 mm×80 mm) of the artificial dura mater obtained in example 2 were embedded in the subcutaneous tissue of a rat back. Each test piece, taken out from the subcutaneous tissue after 1, 2, 3 or 4 weeks, was subjected to tensile strength test. The results are shown in table 3.

TABLE 3

| Dipping period (week) | Tensile strength (kgf) |
|---|---|
| Initial | 1.25 |
| 1 | 1.27 |
| 2 | 0.72 |
| 3 | 0.37 |
| 4 | 0.24 |

As shown in table 3, the results are similar to those of the in vitro degradation test.

As shown above, the artificial dura mater of the invention, which is a substitute of conventional human dura mater, meets all the requirements of non-leakage of cerebrospinal fluid, adequate strength for suture, softness so as not to damage a brain surface, modulus of elasticity close to native dura mater, superior biocompatibility, and biodegradability accompanying repair of damaged tissue. In addition, the artificial dura mater of the invention is transparent so that internal conditions may be observed through the artificial dura mater. The artificial dura mater of the invention, capable of production on an industrial scale, is more inexpensive and stable in quality than lyophilized products of human dura mater.

What we claimed is:

1. An artificial dura mater comprising:
   a sheet made of a copolymer of lactic acid and ε-caprolactone, said copolymer has a molar ratio of about 25–60% of lactic acid and about 75–40% of ε-caprolactone;
   said sheet further includes an integrated reinforcement comprising a fiber component;
   said reinforcement is intervened between a first of said sheet and a second of said sheet made of said copolymer of about 25–60% of lactic acid and about 75–40% of ε-caprolactone; and said fiber component is made of polyglycolic acid.

2. An artificial dura mater comprising:

a sheet made of a copolymer of lactic acid and ε-caprolactone, said sheet further includes an integrated reinforcement comprising a fiber component;

said reinforcement is intervened between a first of said sheet and a second of said sheet made of said copolymer;

said fiber component is made of polyglycolic acid; and said copolymer has a molar ratio of about 50% of lactic acid and about 50% of ε-caprolactone.

* * * * *